US00PP36213P2

(12) United States Plant Patent
Bloodworth

(10) Patent No.: US PP36,213 P2
(45) Date of Patent: Oct. 22, 2024

(54) GRAPEVINE PLANT NAMED 'JB 12-12-A14-29'

(50) Latin Name: ***Vitus rotundifolia* Muscadinia Planch. and *Vitis vinifera***
Varietal Denomination: JB 12-12-A14-29

(71) Applicant: Early Morning LLC, Greendale, IN (US)

(72) Inventor: Patterson Jeffrey Bloodworth, Hillsborough, NC (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 18/491,288

(22) Filed: Oct. 20, 2023

(51) Int. Cl.
*A01H 5/08* (2018.01)
*A01H 6/88* (2018.01)

(52) U.S. Cl.
USPC ..... Plt./206
CPC ..... *A01H 6/88* (2018.05)

(58) Field of Classification Search
USPC ..... Plt./206
CPC ..... A01H 6/88; A01H 5/08
See application file for complete search history.

*Primary Examiner* — Keith O. Robinson
(74) *Attorney, Agent, or Firm* — Weatherly IP Solutions, LLC; James M. Weatherly

(57) ABSTRACT

A new grapevine plant, particularly distinguished by seedless berries borne in well-filled attractive clusters, unlike traditional seeded muscadines, which are marketed as individual berries; relatively thin, more edible skin and juicier flesh compared to most traditional seeded muscadine cultivars; and distinctively flowery and fruity aroma and flavor, making it a top choice in taste panels, disclosed.

3 Drawing Sheets

Genus and species: Intersubgeneric hybrid of *Vitus rotundifolia* Muscadinia Planch. and *Vitis vinifera* Euvitis Planch.
Variety denomination: 'JB 12-12-A14-29'.

BACKGROUND OF THE NEW PLANT

The present invention relates to a new and distinct variety of grapevine hereinafter referred to by the variety name 'JB 12-12-A14-29'.

'JB 12-12-A14-29' arose from a controlled cross in 2012 in Hillsborough, North Carolina, between an unpatented grapevine named 'Summit' female parent and the grapevine named '05-22-3-27' (U.S. Pat. No. 9,045,767) male parent. Seeds and seedlings from the cross were sown and planted in Wasco, California, in 2013, and 'JB 12-12-A14-29' was selected in September 2015.

'JB 12-12-A14-29' was first asexually propagated in Wasco, California, by softwood cuttings. 'JB 12-12-A14-29' was found to reproduce true to type in successive generations of asexual propagation via softwood cuttings.

SUMMARY

The following are the most outstanding and distinguishing characteristics of this new variety when grown under normal horticultural practices in Hillsborough, North Carolina.

1. Seedless berries borne in well-filled attractive clusters, unlike traditional seeded muscadines, which are marketed as individual berries.
2. Relatively thin, more edible skin and juicier flesh compared to most traditional seeded muscadine cultivars, and 3. Distinctively flowery and fruity aroma and flavor, making it a top choice in taste panels.

DESCRIPTION OF THE PHOTOGRAPHS

This new grapevine plant is illustrated by the accompanying photographs, which show the plant's overall plant habit. The colors shown are as true as can be reasonably obtained by conventional photographic procedures.

DESCRIPTION OF THE NEW VARIETY

Figure 1:
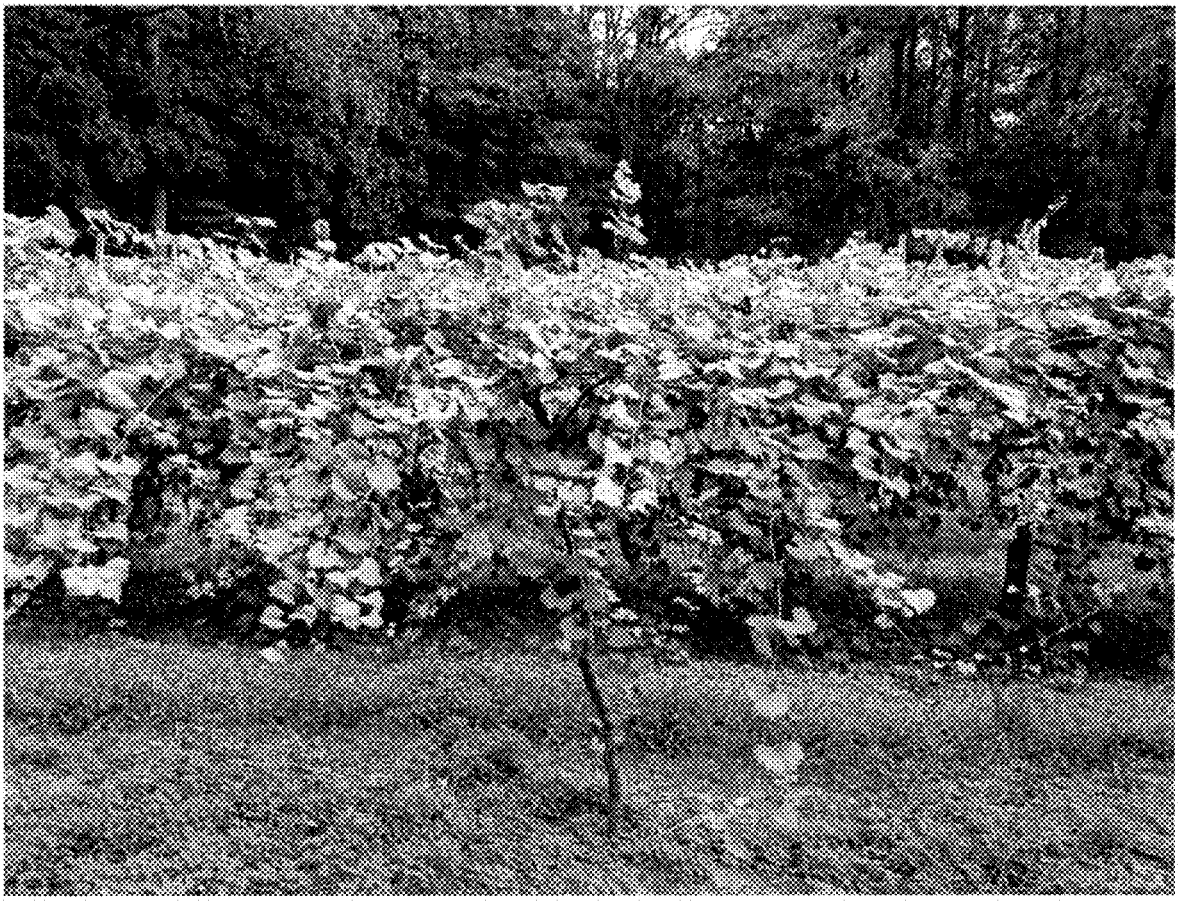
FIG. 1 shows the overall plant and leaves of 'JB 12-12-A14-29' at seven years old, taken in Hillsborough, North Carolina, in October 2023.
Figure 2:
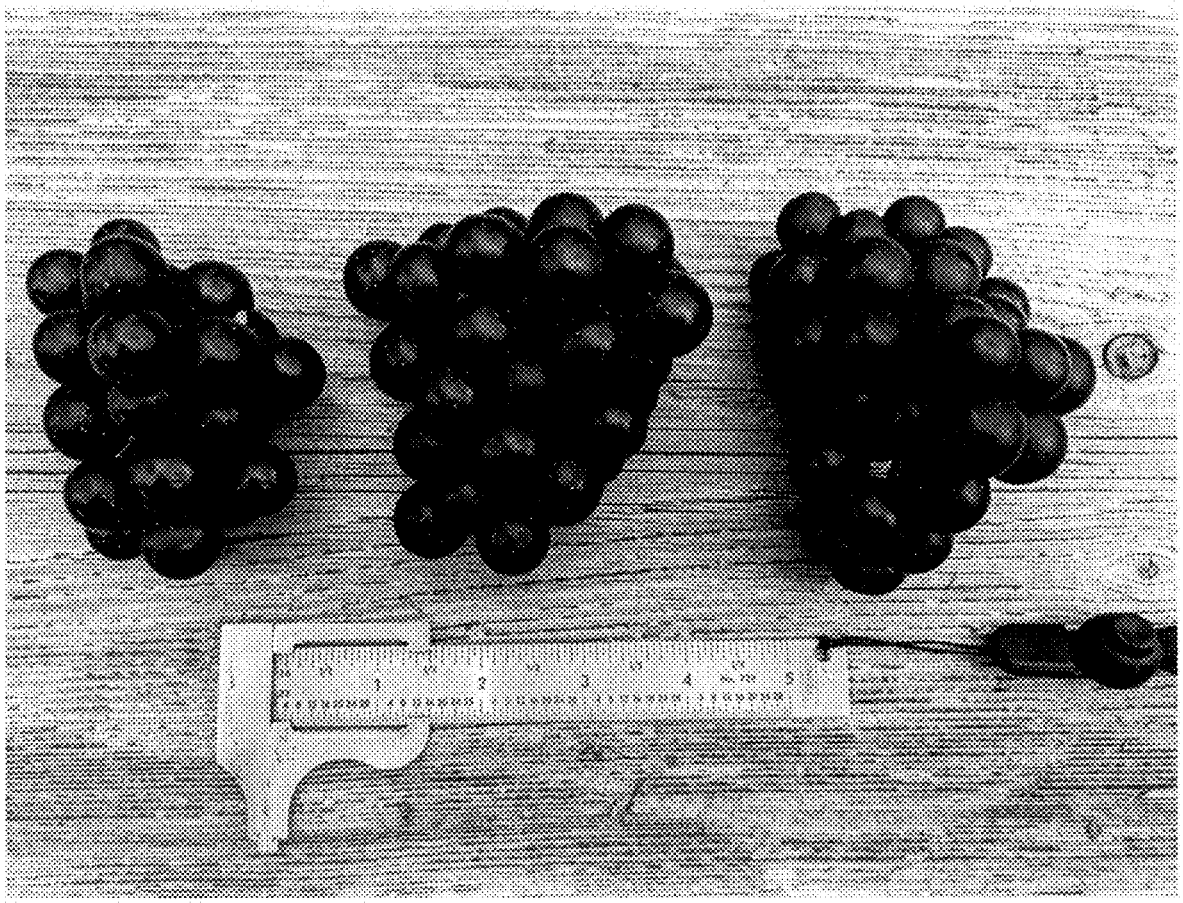
FIG. 2 shows three representative clusters of 'JB 12-12-A14-29'.
Figure 3:
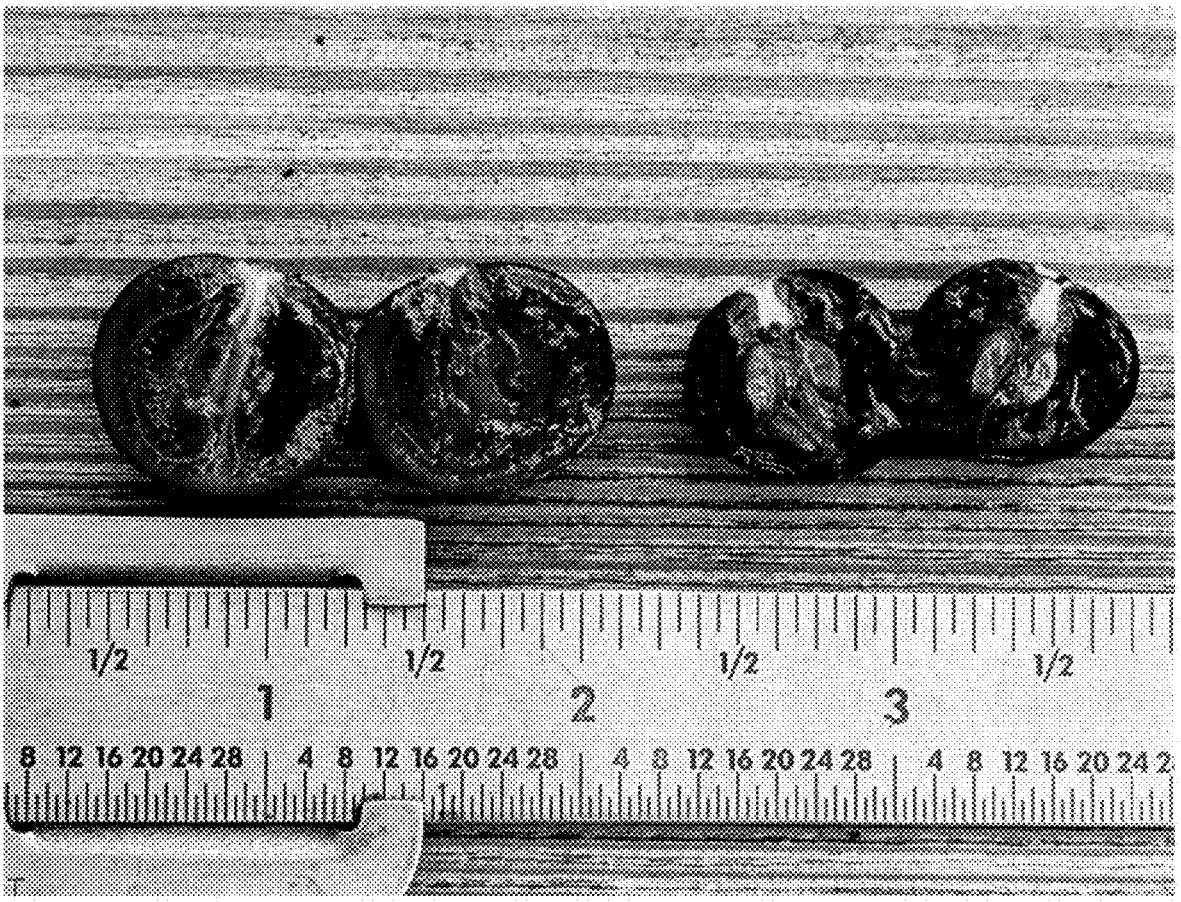
FIG. 3 shows the sectioned fruit of stenospermocarpic seedless 'JB 12-12-A14-29' compared to the seeded commercial variety 'Noble' (unpatented).

The following detailed descriptions are set for the distinctive characteristics of 'JB 12-12-A14-29'. Measurements were taken from three own-rooted vines, two aged seven years old and one aged three years old, observed in the field and under artificial daylight halogen illumination in Hillsborough, North Carolina, from April to September 2023. Color references are to The R.H.S. Colour Chart of The Royal Horticultural Society of London (R.H.S.) 2007, Fifth Edition.

Classification:

*Family*.—Vitaceae.

*Botanical*.—Hybrid between subgenus Muscadinia Planch. (primarily *Vitis rotundifolia*) and subgenus Euvitis Planch. (primarily *Vitis vinifera*, the donor of perfect-floweredness and stenospermocarpic seedlessness).

*Designation*.—'JB 12-12-A14-29'.

Parents:

*Female*.—Summit (unpatented).

*Male*.—'05-22-3-27' (U.S. Pat. No. 9,045,767).

Plant:

*Plant habit and growth*.—Recumbent, climbing, rangy growth with a fairly open canopy.

*Size*.—Large.

*Height*.—6'.

*Width*.—4'.

*Age at maturity*.—3 Years.

*Vigor*.—High.

*Productivity*.—Medium; extrapolated and estimated yield=5.25 tons/acre.

*Cold hardiness/winter hardiness/temperature tolerance*.—2 vines planted in 2016 suffered no apparent winter cold injury after a low temperature of −2° F. in January 2019.

Trunk:

*Diameter*.—1.75" (2016 planting).

*Surface texture*.—Rough.

*Color*.—Old bark RHS 198A, freshly exposed bark RHS 177B.

Canes:

*Diameter*.—Mature, 3rd proximal internode 5/16"× 0.25".

*Length*.—Up to 9'.

*Surface texture*.—Immature cane: Smooth. Mature cane: Slightly rough with raised lenticels.

*Form* (*woody cross-section form*).—Elliptical.

*Color*.—Immature: RHS 146A, 10th internode from apex. Mature: RHS 177B.

*Stem Anthocyanin present*.—Color RHS 165A.

*Internode length* (*upper mature sun cane*).—2.5" up to 4.0".

*Time of bud burst*.—April 11 Swollen buds; April 16 green tissue visible; April 21 fully burst.

*Tendrils*.—Form: Unbranched.

*Size*.—Length: Up to 8". Diameter: 1/32".

*Texture and distribution*.—Smooth, located at node opposite petiole, absent at every 3rd node.

*Color*.—Immature: RHS 152A. Anthocyanin: Present RHS 165A. Mature: RHS 152B. Anthocyanin: yes, RHS 164B.

Growing tips (young shoots):

*Pubescence*.—Present dense, becoming cobwebby on leaves up to 1½ inch across.

*Color*.—RHS 144A.

*Anthocyanin*.—Absent, slight red tinge to pubescence that is mostly colorless, except where underlying leaf anthocyanin is most intensely expressed on very young leaves, interveinally at the basal sinus of leaf dentations, where anthocyanin coloration is variable, from RHS 58A to RHS 58C.

*Shape*.—Shepherd's crook.

*Apex*.—Exposed, the shoot tip is fully open.

Leaves:

*Shape*.—Orbicular, with no deep sinuses. Variation in the length of the dentations may sometimes suggest five indistinct lobes terminating at the ends of the 5 palmately arranged veins.

*Apex*.—Acuminate.

*Base*.—Sagittate.

*Margin*.—Dentate.

*Length of teeth on margin*.—⅛" to ⅜".

*Shape of teeth on margin*.—Straight to flexuous.

*Texture*.—Immature: Upper surface: Smooth. Lower surface: Slightly rough with raised veins. Mature: Upper surface: Smooth. Lower surfaces: Slightly rough with raised veins.

*Size*.—Immature leaf: Length: 2⅞". Width: 2.25". Mature leaf: Length: 4". Width: 4.5".

*Color*.—Immature leaf: Upper surface: RHS 144A. Lower surface: RHS 146B. Mature: Upper surface: RHS N137B. Lower surface: RHS 138B.

*Venation*.—Pattern: Palmate. Color: Upper surface: RHS 146C; Near Petiole RHS 178B. Lower surface: RHS 152B.

Petiolar sinus: Open, lyre shaped.

Petiole:

*Length*.—2" to 3".

*Diameter*.—3/32".

*Color*.—RHS 183A near leaf; RHS 152B Ribs; RHS 143B Grooves.

Floral cluster:

*General description and location*.—panicle, at node, opposite leaf.

*Quantity of florets per cluster*.—223.

*Length*.—2.5".

*Width*.—2⅝".

*Peduncle length*.—⅝" to 1.75".

Inflorescences: Perfect-Flowered.

*Quantity of inflorescences per shoot*.—1-4, normal is 2 per shoot.

*Stamen*.—Form: Upright. Quantity: 7 per floret. Length: 4.5/32".

*Filament*.—Length: 4/32". Color: RHS 193B.

*Anther*.—Shape: Oblong, ovate. Color: RHS 18C.

*Pistil*.—Length: 2.25" to 2.97". Diameter: 1.5" to 1.97". Color: RHS 152A.

*Date of bloom*.—June 16 to June 22, relatively late.

*Pollen amount*.—Abundant.

*Pollen color*.—RHS 18C.

*Calyptra*.—Sheds normally.

*Calyptra color*.—RHS 144C.

Fruit:

*Time of year of commercial harvest and shipment*.—Mid-September.

*Cluster*.—General: Panicle. Size: Large for *V. rotundifolia*, medium-small for *V. vinifera*. Length: Without peduncle: 2¼" to 3¼". Width: 2¼" to 3¼". Density: Well-filled. Shape and weight of cluster: globular to conical w/occasional small wing, 0.6-3.7 oz. Peduncle: Length: ⅝" to 1¾". Diameter: 2/32" to 3/32". Color: RHS 165A. Number of berries per cluster: Up to 53.

*Berry*.—Size: Small to medium. Shape: Spherical. Length: ½" to ¾" mean is ⅝". Diameter (width): ½" to ¾" mean is ⅝". Uniformity: Acceptably uniform. Ripening: September 15, which is mid-season. Skin: Type: Slip Skin. Color: RHS 203B. Lenticels: Sparse to medium in density, minute up to 1/32" in diameter, color RHS 172A. Thickness: 1/16" as peeled manually from flesh. Texture: Crunchy, tender, fragmenting readily, non-astringent. Waxy bloom: Very slight, not readily noticeable. Weight of individual berry: Mean is 3.05 g up to 5.0 g.

*Pedicel*.—Length: 3/32 to 1/8". Diameter: 3/64" in middle. Color: RHS N199B. Strength of attachment to berry: Strong, detaches with wet scar, occasionally with attached broken pedicel.

*Flesh*.—Color: RHS 150D translucent. Juice color: RHS 155D clear. Juice production: Moderate to high. Texture: Mucilaginous, reduces largely into juice. Brix Content: 19.1° Flavor: Very fruity, non-musky. Fragrance: Very flowery to fruity, non-musky.

Seed traces:

*Size*.—Minute to small.

*Length*.—Up to 1/16".

*Width*.—Up to 1/32".

*Texture*.—Soft.

*Perception*.—Unnoticeable.

Disease and insect resistance: 'JB 12-12-A14-29' often displays leaf spot symptoms which resemble angular leaf spot caused by the fungus *Mycosphaerella angulata* Jenkins. This condition has been diagnosed as edema, a physiological disorder which is more marked in vines planted in lower, wetter soils. These leaf spot symptoms are not extensive and do not appear to significantly affect overall vine health. Both parents of 'JB 12-12-A14-29' are thought to be highly resistant to the muscadine form of black rot (BRM) caused by *Guignardia bidwellii* f. *muscadinii* Lutrell. 'JB 12-12-A14-29' has always been grown with fungicidal protection so actual resistance to BRM is not known. Both parents of 'JB 12-12-A14-29' are highly resistant to berry rots which commonly affect muscadine grapes. Berry rots have never been seen on 'JB 12-12-A14-29'.

Cultural note: Skin cracking on ripe berries after significant rainfall has occasionally been observed but does not appear to be extensive. Fruit set may be adversely affected by excessive shoot vigor, so nitrogen fertilizers should be applied judiciously. Bud break on canes is spotty and less than complete, so 'JB 12-12-A14-29' should be pruned to short spurs.

COMPARISON WITH PARENTAL LINES AND KNOWN VARIETY

'JB 12-12-A14-29' is a distinct variety of grapevine and is distinguished from its parents as described in Table 1:

TABLE 1

Comparison with the Parental Lines

| Trait | Variety 'JB 12-12-A14-29' | Female parent 'Summit' | Male Parent 'JB05-22-3-27' |
|---|---|---|---|
| Fruit color | Black | Bronze | Red/Purple |
| Seed | Seedless | Seeded | Seedless |
| Sex | Perfect-flowered | Female | Perfect-flowered |

'JB 12-12-A14-29' is most similar to the commercial grapevine variety 'Noble' (unpatented). Differences between the varieties are described in Table 2.

TABLE 2

Comparison with Commercial Line

| Characteristic | 'JB 12-12-A14-29' | Commercial line 'Noble' |
|---|---|---|
| Seed | Seedless | Seeded |

I claim:

1. A new and distinct cultivar of Grapevine Plant Named 'JB 12-12-A14-29' as described and illustrated herein.

* * * * *